(12) United States Patent
Gomez-de-Diego

(10) Patent No.: US 7,276,040 B2
(45) Date of Patent: Oct. 2, 2007

(54) TRACTION APPARATUS FOR THE PENIS

(76) Inventor: Eduardo Gomez-de-Diego, C/ Princessa 22, 6 cha, Madird (ES) 28008

( * ) Notice: Subject to any disclaimer, the term of this patent is extended or adjusted under 35 U.S.C. 154(b) by 510 days.

(21) Appl. No.: 10/829,006

(22) Filed: Apr. 21, 2004

(65) Prior Publication Data

US 2004/0215055 A1    Oct. 28, 2004

(30) Foreign Application Priority Data

Apr. 28, 2003    (EP) .................................. 03380101

(51) Int. Cl.
*A61F 5/00*    (2006.01)
(52) U.S. Cl. .......................................... 602/36; 600/39
(58) Field of Classification Search .................. 602/36; 600/38, 39, 41; 128/842
See application file for complete search history.

(56) References Cited

FOREIGN PATENT DOCUMENTS

WO    WO9626691    *    9/1996

* cited by examiner

*Primary Examiner*—Kim M. Lewis
(74) *Attorney, Agent, or Firm*—Allen, Dyer, Doppelt, Milbrath & Gilchrist, P.A.

(57) ABSTRACT

An apparatus and method for applying traction to a patient's penis includes at least one base member having a generally arcuate or circular periphery of sufficient dimension for the patient to insert the penis in the apparatus. At least one base member connector is positioned on the base member. A plurality of extension members is connected with the base member connector and extends distally therefrom so that at least one support member connected with the plurality of extension members is distally spaced apart from the base member, the support member having a surface for thereon supporting the penis. A retaining collar connected to the support member adjacent the support surface is positioned so as to at least partially encircle the shaft of the penis thereby securing the distal penis to the support member.

37 Claims, 4 Drawing Sheets

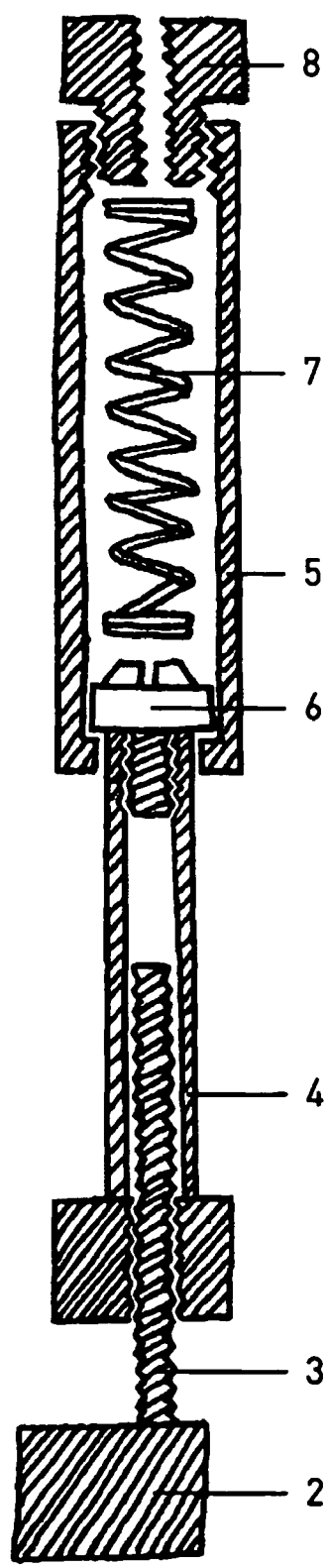
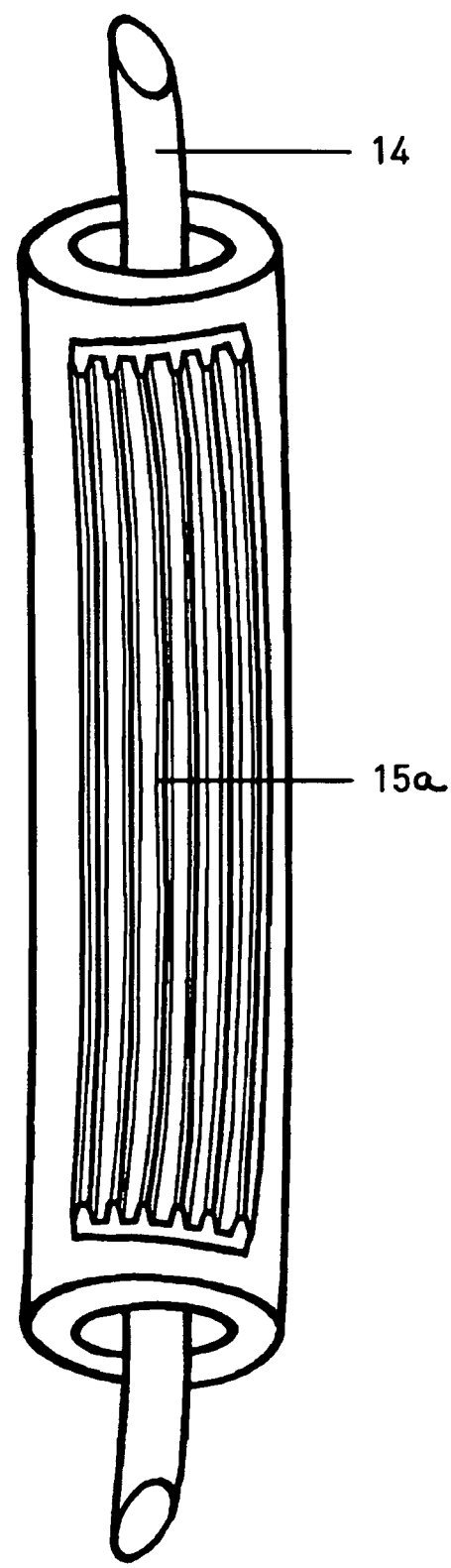
FIG. 4  FIG. 5

TRACTION APPARATUS FOR THE PENIS

RELATED APPLICATION

This application claims foreign priority from Application No. 03380101.0, which was filed in Europe through the Spanish Patent Office on Apr. 28, 2003, and which application is incorporated herein by reference in its entirety.

FIELD OF THE INVENTION

The present invention relates to the field of traction devices and, more particularly, to an apparatus for applying traction to the human penis.

BACKGROUND OF THE INVENTION

Since about 1905 it has been known to use tissue traction for stretching parts of the body, and in approximately 1957 Neuman performed tissue expansion in practice. Traction of fingers was first described by the American investigator Cowen who, at the annual U.S. Congress of Orthopedic Surgery in 1977, spoke about stretching fingers to normal length in children who had been born with too short fingers. On the basis of his clinical work Cowen reported that blood vessels and all other tissues on the extremity are stretched, provided that the rate of traction does not exceed the rate of nerve regeneration.

Animal experiments have shown that the epidermis responds to constant expansion or tension by increasing cell division activity in the basal layer, a process which reaches a maximum rate within about 24-48 hours and typically normalizes within 6 days. These animal experiments have also shown that expansion of the dermis tends to reduce its thickness slightly. However, normalization of the thickness of the dermis following expansion has been reported after about two years.

SUMMARY OF THE INVENTION

With the foregoing in mind, the present invention advantageously provides an apparatus and a method of applying traction to the male penis. It should be understood that the apparatus is preferably intended for use with a human penis which includes normal parts such as a shaft, a glans, and a corona glandis.

The apparatus comprises at least one base member having a generally arcuate periphery of sufficient dimension for the patient to insert the penis in the apparatus. More preferably, the base member comprises an annular base member having a generally circular periphery and an opening of sufficient dimension for the patient to insert the penis therethrough. At least one base member connector is positioned on the at least one base member. The base member connector serves to connect with a plurality of extension members which will extend distally from the base member. At least one support member is connected with the plurality of extension members and is thereby distally spaced apart from the at least one base member, the at least one support member having a surface for thereon supporting a distal portion of the penis. A retaining collar is connected to the support member adjacent the support surface and is positioned so as to at least partially encircle the shaft of the penis and engage the corona glandis thereby securing the distal penis to the support member.

From the start, a method of the invention includes providing an annular base member having generally circular periphery and an opening of sufficient dimension for the patient to insert the penis in the apparatus. The method then involves hingedly connecting two base member connectors to and extending from the annular base member, and connecting a plurality of extension members to the two base member connectors so that the plurality of extension members extends away from the two base member connectors. A support member is positioned connected to the plurality of extension members so as to be a distance spaced apart from the annular base member. The support member has an arcuate support surface for thereon supporting the penis. The method then calls for inserting the patient's penis through the annular base member so as to rest a distal portion of the shaft upon the arcuate support surface, and positioning a retaining collar adjacent the support surface adjustably connected to the support member to secure the distal penis to the support member by at least partially surrounding the shaft of the patient's penis, or by engaging the corona glandis. Finally, the method continues by applying traction to the penis by increasing the spaced apart distance between the annular base member and the support member. Thereafter, the method stops.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which:

FIG. 4 shows a detailed cross sectional view of an embodiment of a base member connector in the apparatus of FIG. 1;

FIG. 5 depicts a view of the retaining retaining collar of the apparatus when not in use as shown in FIG. 1.

DETAILED DESCRIPTION OF THE PREFERRED EMBODIMENT

Figure 1:
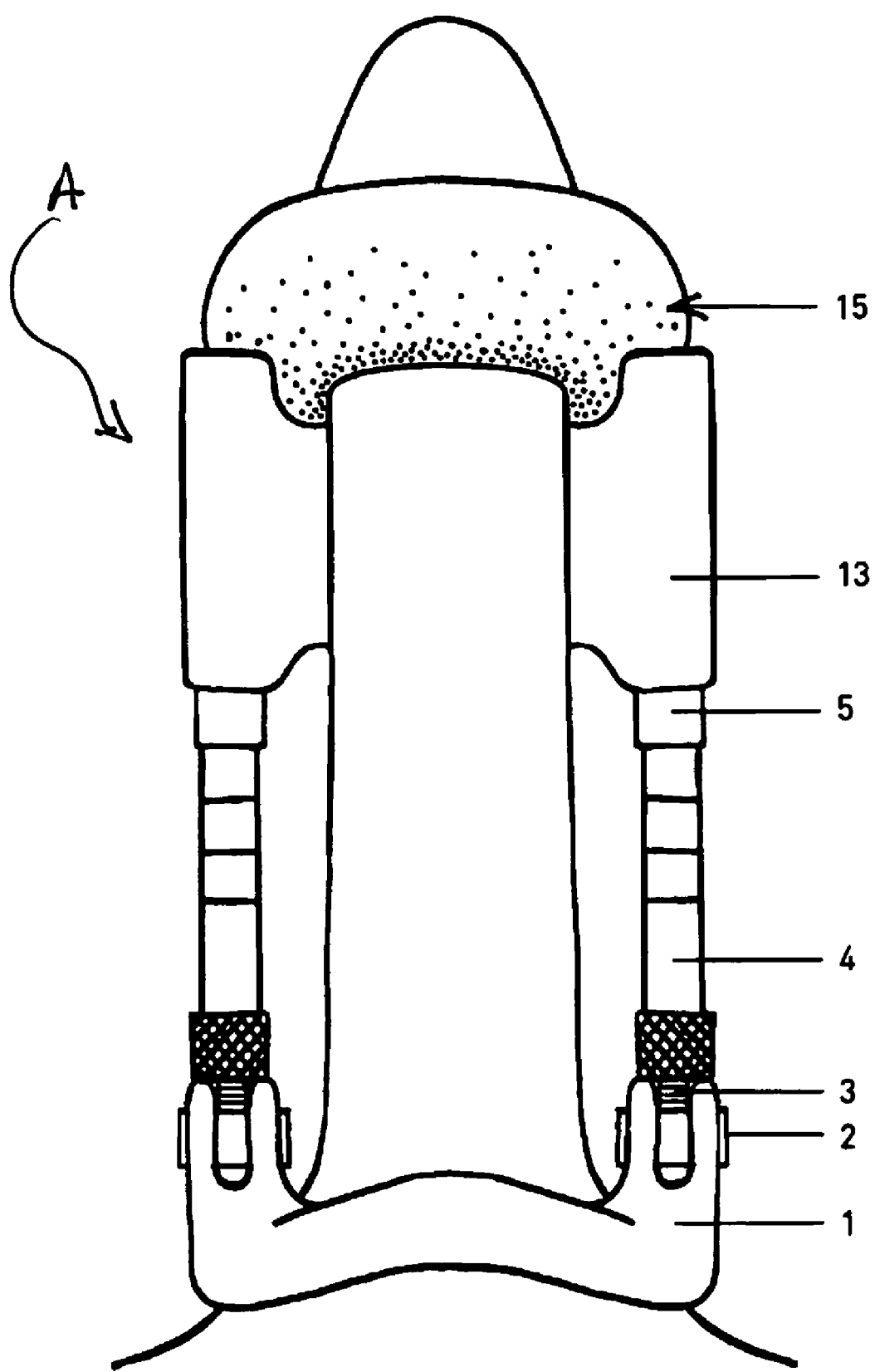
FIG. 1 is an overall top plan view of the apparatus of the present invention in use to apply traction to a patient's penis.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

FIGS. 1-5 illustrate an apparatus for applying traction to a patient's penis according to the present invention. It should be understood that the present apparatus is preferably intended for use on a penis having normal component parts such as a shaft, a glans, and a corona glandis, although the device may also be applied to abnormally formed organs.

The apparatus A comprises at least one base member 1 having a generally arcuate periphery of sufficient dimension for the patient to insert the penis in the apparatus. More preferably, the base member 1 comprises an annular base member having generally circular periphery and an opening of sufficient dimension for the patient to insert the penis in the apparatus. At least one base member connector 2-7 is positioned on the base member 1. A plurality of extension members 8-12 is connected with the base member connector and extends distally therefrom. At least one support member 13 is connected with the plurality of extension members 8-12 and is thereby distally spaced apart from the at least one base member 1, the support member having a support surface for thereon supporting the penis, preferably an arcuate surface. A retaining collar 15 is connected to the support member 13 adjacent the support surface 5 and is positioned so as to at least partially encircle the shaft of the penis thereby securing the distal penis to the support member. The retaining collar 15 may also be adjustably connected to the support member 13 to engage the corona glandis C so as to secure the distal penis to the support member. Preferably, the collar 15 functions both by encircling the shaft of the penis, at least partially, and by engaging the corona glandis so as to prevent the distal penis from being withdrawn from contact with the support member 13. In the invention, the periphery of the at least one base member 1 is preferably approximately complementary to a pubic mound, so that the base member may be worn by a patient comfortably abutting the pubic mound.

Figure 2:
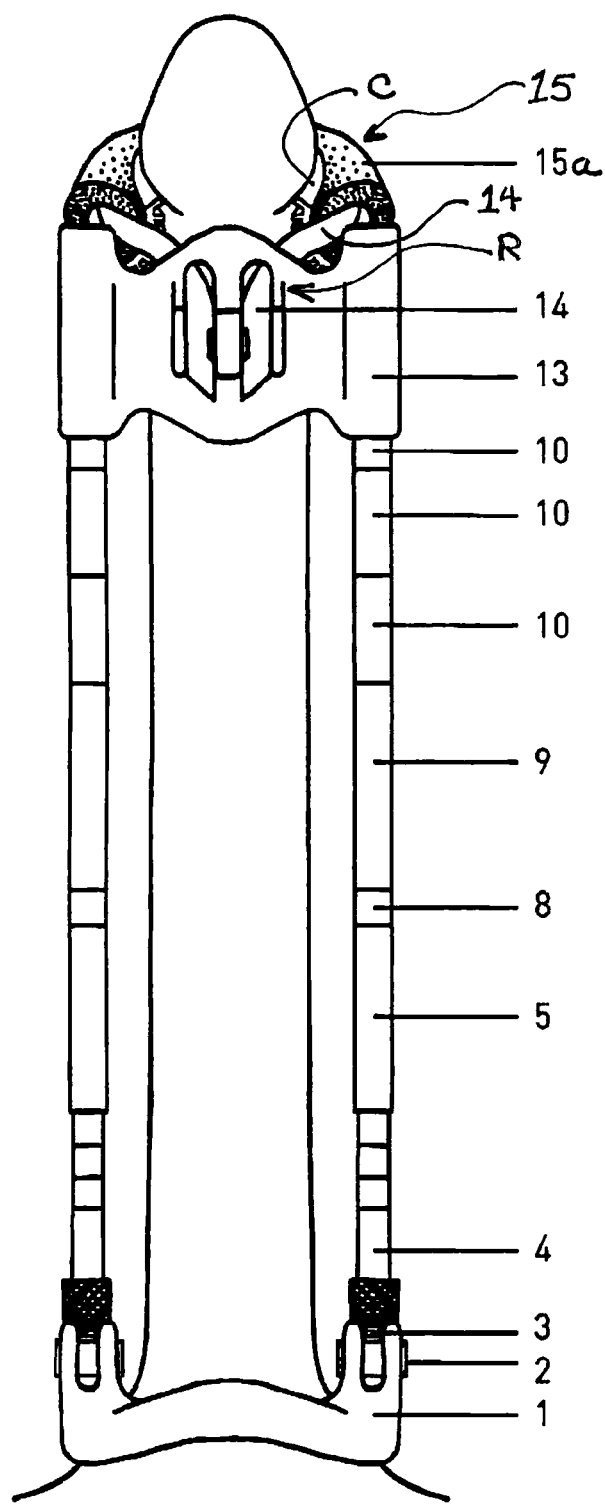
FIG. 2 is a bottom plan view of an apparatus according to FIG. 1 but with additional extension members in use.

The plurality of base member connectors comprises connectors 2-7 extending outwardly from the periphery of the base member and approximately perpendicular to an imaginary diameter of the base member. The base member connector 2-7 most preferably comprises a hinged connector extending outwardly from the generally arcuate periphery of the at least one base member so that an angle of connection of the base member connector 2-7 to the base member may be adjusted, allowing the apparatus to be worn by a patient during his routine daily activities. The skilled will appreciate the adjustability of the angle of the base member connector 2-7 by noting the engagement relationship between knob 2 and base member 1. as shown in FIGS. 1 and 2.

As shown in FIG. 4, the base member connector 2-7 is adjustable in length in small increments by turning the piston 4 upon threaded connector 3. As can be seen, the base member connector comprises a knob 2 having a threaded connector 3 engaged with a complementary threaded piston 4, the piston being also slidably disposed within a cylinder 5 at a first cylinder end and held therein by piston cap 6. The cylinder 5 has therein a biasing member 7 which urges against the piston 4, and has at a second cylinder end threads complementary to at least one individual extension member 8 of the plurality of extension members. As shown in FIG. 4, the base member connector 2-7 aids in maintaining a degree of tension in the traction apparatus A by the action of the biasing member 7 against the piston 4 in the cylinder 5.

Figure 3:
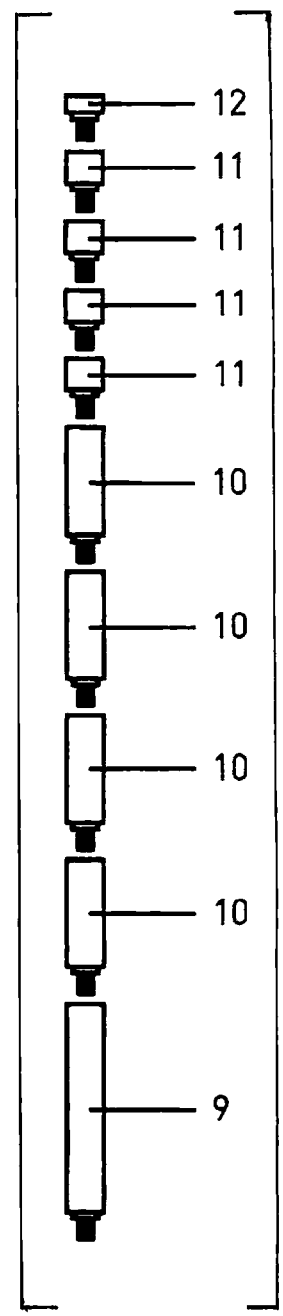
FIG. 3 shows an exploded view of a plurality of extension members for use in the apparatus of FIG. 1.

The plurality of extension members 8-12 includes individual extension members having different lengths, as shown in FIG. 3, wherein are seen long extension members 9, medium length extension members 10, short extension members 11, and very short extension members 12. As shown, extension members 8-12 are preferably threaded, having both male and female threaded connectors for coupling with each other, with the base member connector 2-7, and with the support member 13. Other connection mechanisms may also be employed in the invention, however, for example snap connections or any other mechanisms as known to the skilled. It should be appreciated that in the invention, the plurality of extension members 8-12 comprises a sufficient number of individual extension members to extend the apparatus A to apply traction to the patient's penis by increasing the distance between the base member and the retaining collar.

In the apparatus A, the support surface of the support member 13 comprises a generally curved surface for thereon supporting the patient's penis. More preferably, the support member 13 comprises a generally curved member having at least one dimension approximately equal to an imaginary diameter of the arcuate periphery of the at least one base member. The support member 13 may also comprise first and second ends and a curved surface therebetween, the first and second ends spaced apart a distance approximately equal to an imaginary diameter of the arcuate or circular periphery of the at least one base member 1. The support member may 13 additionally comprise at least one receiver R for receiving at least a portion of the retaining collar 15 to thereby secure the retaining collar to the support member.

The retaining collar 15 preferably comprises a relatively soft and resilient retaining member, as illustrated in FIGS. 1, 2 and 5. The retaining collar 15 comprises an outer, relatively soft retaining member 15a and an inner elastic member 14, a detailed view of this arrangement being shown in FIGS. 2 and 5. As shown in FIG. 5. the retaining collar 15 in a preferred embodiment includes the relatively soft retaining member being a tubular outer member 15a and having an elastic inner member 14 extending therethrough, the elastic inner member having first end and a second ends, both of which protrude from the tubular outer member. The retaining collar 15 shown in FIG. 5 may be secured to the support member 13 by adjustably connecting the protruding first and second ends to the at least one support member, by engaging the ends in the receiver R, which as shown in FIG. 2 includes two slots cut on an underside of the support member 13.

Figure 6:
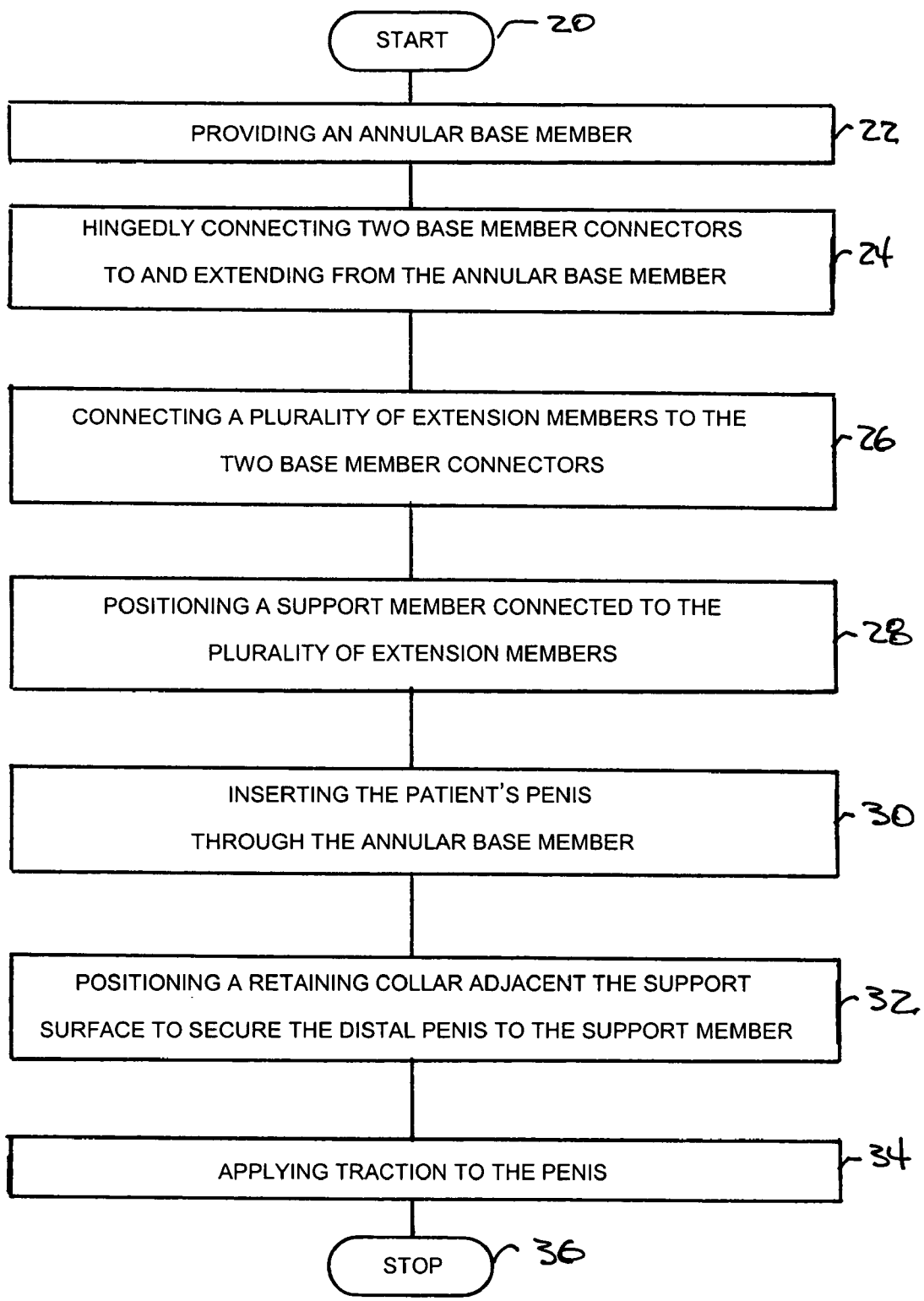
FIG. 6 is a flow diagram illustrating a method of the invention of FIG. 1.

The present invention also includes various method aspects which are shown in the block diagram of FIG. 6. The method is for applying traction to a patient's penis having a shaft, a glans, and a corona glandis. From a start 20, the method includes providing 22 an annular base member having generally circular periphery and an opening of sufficient dimension for the patient to insert the penis in the apparatus. The method continues by hingedly connecting 24 two base member connectors to and extending from the annular base member, and connecting 26 a plurality of extension members to the two base member connectors so that the plurality of extension members extends away from the two base member connectors. The method also requires positioning 28 a support member connected to the plurality of extension members so as to be a distance spaced apart from the annular base member, the support member having an arcuate support surface for thereon supporting the penis. The method calls for inserting the patient's penis 30 through the annular base member so as to rest a distal portion of the shaft upon the arcuate support surface, and positioning 32 a retaining collar adjacent the support surface to at least partially surround the shaft of the patient's penis, the retaining collar adjustably connected to the support member to thereby engage the corona glandis thereby securing the distal penis to the support member. Finally, the method includes applying traction 34 to the penis by increasing the spaced apart distance between the annular base member and the support member. Thereafter, the method stops 36. It should be understood, however, that in alternate embodiments of the method, applying traction may be continued for a predetermined length of time.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. An apparatus for applying traction to a patient's penis having a shaft, a glans, and a corona glandis, the apparatus comprising:
    at least one base member having a generally arcuate periphery of sufficient dimension for the patient to insert the penis in the apparatus;
    at least one base member connector positioned on said at least one base member;
    one or more extension members of predetermined lengths connected with said at least one base member connector and extending distally therefrom;
    at least one support member connected with said plurality of extension members and thereby being distally spaced apart from said at least one base member, said at least one support member having a surface for thereon supporting the penis; and
    a retaining collar connected to said at least one support member adjacent said support surface and positioned so as to at least partially encircle the shaft of the penis thereby securing the distal penis to the support member.

2. The apparatus of claim 1 wherein the generally arcuate periphery of said at least one base member is approximately complementary to a pubic mound.

3. The apparatus of claim 1, wherein the at least one base member connectors comprises connectors extending outwardly from the generally arcuate periphery of said at least one base member and approximately perpendicular to an imaginary diameter thereof.

4. The apparatus of claim 1, wherein said at least one base member connector comprises a hinged connector extending outwardly from the generally arcuate periphery of said at least one base member so that an angle of connection of said at least one base member connector to the at least one base member may be adjusted.

5. The apparatus of claim 1, wherein said at least one base member connector comprises a knob having a threaded connector engaged with a complementary threaded piston, said piston being slidably disposed within a cylinder at a first cylinder end, said cylinder having therein a biasing member urging against said piston, and having at a second cylinder end threads complementary to at least one individual extension member of said plurality of extension members.

6. The apparatus of claim 1, wherein said one or more extension members comprise individual extension members having different predetermined lengths.

7. The apparatus of claim 1, wherein said one or more extension members comprises individual extension members threadingly connectable to each other.

8. The apparatus of claim 1, wherein said one or more extension members threadingly connect to said at least one base member and to said at least one support member.

9. The apparatus of claim 1, wherein said one or more extension members comprise a sufficient number of individual extension members to extend said apparatus to apply traction to the patient's penis by increasing distance between said at least one base member and said retaining collar.

10. The apparatus of claim 1, wherein the surface on said at least one support member comprises a generally curved surface for thereon supporting the patient's penis.

11. The apparatus of claim 1, wherein said at least one support member comprises a generally curved member having at least one dimension approximately equal to an imaginary diameter of the arcuate periphery of said at least one base member.

12. The apparatus of claim 1, wherein said at least one support member comprises first and second ends and a curved surface therebetween, said first and second ends spaced apart a distance approximately equal to an imaginary diameter of the arcuate periphery of said at least one base member.

13. The apparatus of claim 1, wherein said at least one support member comprises at least one receiver for receiving at least a portion of said retaining collar to thereby secure the retaining collar to the at least one support member.

14. The apparatus of claim 1, wherein said retaining collar comprises a relatively soft and resilient retaining member.

15. The apparatus of claim 1, wherein said retaining collar comprises an outer relatively soft retaining member and an inner elastic member.

16. The apparatus of claim 1, wherein said retaining collar comprises a tubular outer member and an elastic inner member extending therethrough.

17. The apparatus of claim 16, wherein said elastic inner member has a first end and a second end, both of which protrude from said tubular outer member.

18. The apparatus of claim 17, wherein said retaining collar is secured to said at least one support member by adjustably connecting the protruding first and second ends to the at least one support member.

19. An apparatus for applying traction to a patient's penis having a shaft, a glans, and a corona glandis, the apparatus comprising:
    an annular base member having generally circular periphery and an opening of sufficient dimension for the patient to insert the penis in the apparatus;
    two base member connectors hingedly connected to and extending from said annular base member;
    a plurality of extension members of predetermined lengths connected with said two base member connectors so as to extend away therefrom;
    a support member connected to said plurality of extension members so as to be spaced apart from said annular base member, said support member having an arcuate surface for thereon supporting the penis; and
    a retaining collar positioned abutting said support member adjacent said support surface, said retaining collar being adjustably connected to the support member to thereby engage the corona glandis thereby securing the distal penis to the support member.

20. The apparatus of claim 19, wherein generally circular periphery of said annular base member is approximately complementary to a pubic mound.

21. The apparatus of claim 19, wherein said two base member connectors comprise connectors extending outwardly from the generally circular periphery of said annular base member and are approximately perpendicular to an imaginary diameter thereof.

22. The apparatus of claim 19, wherein said two base member connectors comprise hinged connectors extending outwardly from the generally circular periphery of said annular base member so that an angle of connection of said two base member connectors to said annular base member is adjustable.

23. The apparatus of claim 19, wherein said at least one base member connector comprises a knob having a threaded connector engaged with a complementary threaded piston, said piston being slidably disposed within a cylinder at a first cylinder end, said cylinder having therein a biasing member urging against said piston, and having at a second cylinder end threads complementary to at least one individual extension member of said plurality of extension members.

24. The apparatus of claim 19, wherein said plurality of extension members comprises individual extension members having different predetermined lengths.

25. The apparatus of claim 19, wherein said plurality of extension members comprises individual extension members which are threadingly connectable to each other.

26. The apparatus of claim 19, wherein said plurality of extension members threadingly connects to said two base members and to said support member.

27. The apparatus of claim 19, wherein said plurality of extension members comprises a sufficient number of individual extension members to extend said apparatus to apply traction to the therein inserted patient's penis by increasing distance between said annular base member and said retaining collar.

28. The apparatus of claim 19, wherein said support member comprises a generally curved member having at least one dimension approximately equal to an imaginary diameter of the generally circular periphery of said annular base member.

29. The apparatus of claim 19, wherein said support member comprises first and second ends and said arcuate surface is positioned therebetween, said first and second ends being spaced apart a distance approximately equal to an imaginary diameter of the generally circular periphery of said at least one base member.

30. The apparatus of claim 19, wherein said support member comprises at least one receiver for receiving at least a portion of said retaining collar to thereby secure said retaining collar to said support member.

31. The apparatus of claim 19, wherein said retaining collar comprises a relatively soft resilient retaining material.

32. The apparatus of claim 19, wherein said retaining collar comprises an outer relatively soft material and an inner elastic material.

33. The apparatus of claim 19, wherein said retaining collar comprises a tubular outer material and an elastic inner material extending therethrough.

34. The apparatus of claim 33, wherein said elastic inner material has a first end and a second end, both of which protrude from said tubular outer material.

35. The apparatus of claim 34, wherein said retaining collar is secured to said support member by adjustably connecting the protruding first and second ends of the elastic inner material to said support member.

36. A method of applying traction to a patient's penis having a shaft, a glans, and a corona glandis, the method comprising:
   providing an annular base member having generally circular periphery and an opening of sufficient dimension for the patient to insert the penis in the apparatus;
   hingedly connecting two base member connectors to and extending from said annular base member;
   connecting a plurality of extension members of predetermined lengths to said two base member connectors so that the plurality of extension members extends away from the two base member connectors;
   positioning a support member connected to said plurality of extension members so as to be a distance spaced apart from said annular base member, said support member having an arcuate support surface for thereon supporting the penis;
   inserting the patient's penis through the annular base member so as to rest a distal portion of the shaft upon the arcuate support surface;
   positioning a retaining collar adjacent said support surface to at least partially surround the shaft of the patient's penis, the retaining collar adjustably connected to the support member to thereby engage the corona glandis thereby securing the distal penis to the support member; and
   applying traction to the penis by increasing the spaced apart distance between the annular base member and the support member.

37. The method of claim 36, wherein applying traction is continued for a predetermined length of time.

\* \* \* \* \*